US008956996B2

(12) United States Patent
Gewehr et al.

(10) Patent No.: US 8,956,996 B2
(45) Date of Patent: Feb. 17, 2015

(54) METHOD FOR REDUCING NITROUS OXIDE EMISSION FROM SOILS

(75) Inventors: Markus Gewehr, Kastellaun (DE); Ansgar Wille, Neustadt (DE); Christina Geiger, Mannheim (DE); Hans-Jürgen Lutz, Freinsheim (DE); Lutz Brahm, Worms (DE); Alexander Wissemeier, Speyer (DE); Dana Peach, Raleigh, NC (US); Barbara Nave, Ruppertsberg (DE)

(73) Assignee: BASF SE, Ludwigshafen (DE)

( * ) Notice: Subject to any disclaimer, the term of this patent is extended or adjusted under 35 U.S.C. 154(b) by 60 days.

(21) Appl. No.: 13/496,218

(22) PCT Filed: Sep. 13, 2010

(86) PCT No.: PCT/EP2010/063358
§ 371 (c)(1),
(2), (4) Date: May 30, 2012

(87) PCT Pub. No.: WO2011/032904
PCT Pub. Date: Mar. 24, 2011

(65) Prior Publication Data
US 2012/0252668 A1    Oct. 4, 2012

(30) Foreign Application Priority Data
Sep. 16, 2009   (EP) ..................................... 09170414

(51) Int. Cl.
| *A01N 59/04* | (2006.01) |
| *A01N 43/54* | (2006.01) |
| *A01N 25/00* | (2006.01) |
| *A01N 35/04* | (2006.01) |
| *A01N 37/50* | (2006.01) |
| *A01N 43/40* | (2006.01) |
| *A01N 43/56* | (2006.01) |
| *A01N 43/653* | (2006.01) |
| *A01N 47/02* | (2006.01) |
| *A01N 47/24* | (2006.01) |
| *A01N 51/00* | (2006.01) |
| *A01N 61/00* | (2006.01) |
| *C05C 1/00* | (2006.01) |
| *C05G 3/02* | (2006.01) |

(52) U.S. Cl.
CPC ................ *A01N 43/54* (2013.01); *A01N 25/00* (2013.01); *A01N 35/04* (2013.01); *A01N 37/50* (2013.01); *A01N 43/40* (2013.01); *A01N 43/56* (2013.01); *A01N 43/653* (2013.01); *A01N 47/02* (2013.01); *A01N 47/24* (2013.01); *A01N 51/00* (2013.01); *A01N 61/00* (2013.01); *C05C 1/00* (2013.01); *C05G 3/02* (2013.01)
USPC ....................................................... 504/101

(58) Field of Classification Search
CPC ....... A01N 47/24; A01N 37/50; A01N 47/02; A01N 61/00; A01N 43/653; A01N 51/00; A01N 35/04; C05C 1/00; C05G 3/02
See application file for complete search history.

(56) References Cited

U.S. PATENT DOCUMENTS

2008/0293798 A1*   11/2008   Dietz et al. .................... 514/407

FOREIGN PATENT DOCUMENTS

| CA | 2262617 | 2/1998 |
| CA | 2454542 | 2/2003 |
| WO | WO 98/05607 | 2/1998 |
| WO | WO 03/009687 | 2/2003 |
| WO | WO 2008/092819 | 8/2008 |
| WO | WO 2008/129060 | 10/2008 |

OTHER PUBLICATIONS

International Search Report, PCT/EP2010/063358, Jan. 14, 2011.
International Preliminary Report on Patentability, PCT/EP2010/063358, Mar. 20, 2012.
Basf et al., "Safety data sheet. Pristine®", Version 1.6, Internet Citation, Feb. 1, 2008, pp. 1-8, XP007912929, Search Report.
Chandra et al., "Effects of Nabam and Mylone on Nitrification, Soil Respiration, and Microbial Numbers in Four Oregon Soils", Soil Science, vol. 92, Jan. 1, 1961, pp. 387-393, XP009140013, Search Report.
Dharnaraj, "Effects of pesticides on nitrification and denitrification", Pesticides and Nitrogen Cycle, vol. II, Jan. 1, 1988, pp. 43-118, XP009133062, Search Report.
Dubey, "A Nitrogen Deficiency Disease of Sugarcane Probably Caused by Repeated Pesticide Applications", Phytopathology, vol. 60, Mar. 1, 1970, pp. 485-487, XP007915372, Search Report.
Kinney et al., "Effects of the fungicides mancozeb and chlorothalonil on fluxes of $CO_2$, $N_2O$, and $CH_4$ in a fertilized Colorado grassland soil", Journal of Geophysical Research, vol. 109, Mar. 4, 2004, pp. 1-15.
Kinney et al., "Laboratory investigations into the effects of the pesticides mancozeb, chlorothalonil, and prosulfuron on nitrous oxide and nitric oxide production in fertilized soil", Soil Biology & Biochemistry, vol. 37, No. 5, May 1, 2005, pp. 837-850, XP025362491, Search Report.
Macadam et al., "Dicyandiamide and 3,4-dimethyl pyrazole phosphate decrease $N_2O$ emissions from grassland but dicyandiamide produces deleterious effects in clover", Journal of Plant Physiology, vol. 160, No. 12, Jan. 1, 2003, pp. 1517-1523, XP004955566, Search Report.
Mosier et al., "Nitrous oxide emissions from agricultural fields: Assessment, measurement and mitigation", Plant and Soil, vol. 181, 1996, pp. 95-108.

(Continued)

*Primary Examiner* — Abigail Fisher
*Assistant Examiner* — Daniel L Branson
(74) *Attorney, Agent, or Firm* — Brinks Gilson & Lione

(57) ABSTRACT

The present invention relates to a method for reducing nitrous oxide emission from soils comprising treating a plant growing on the respective soil and/or the locus where the plant is growing or is intended to grow and/or the seeds from which the plant grows with at least one fungicide (compound A) and at least one ammonium- or urea-containing fertilizer (compound B) wherein the application of at least one compound (A) and at least one compound (B) is carried out with a time lag of at least 1 day.

11 Claims, No Drawings

(56) References Cited

OTHER PUBLICATIONS

Somda et al., "Influence of Biocides on Tomato Nitrogen Uptake and Soil Nitrification and Denitrification", Journal of Plant Nutrition, vol. 14, Nov. 11, 1991, pp. 1187-1199.

Tilman et al., "Forecasting Agriculturally Driven Global Environmental Change", Science, vol. 292, Apr. 13, 2001, pp. 281-284.

Tomlin (Editor), "584 Nabam", The Pesticide Manual, 14$^{th}$ Ed., Jan. 1, 2006, XP002605513, Search Report.

"Ullmann's Agrochemicals", Jan. 1, 2007, Wiley-VCH, pp. 56-61, 130-131, XP002581804, Search Report.

Chain, Patrick et al., "Complete Genome Sequence of the Ammonia-Oxidizing Bacterium and Obligate Chemolithoautotroph *Nitrosomonas europaea*", *Journal of Bacteriology*, (May 2003) vol. 185(9):2759-2773.

Feil, Helene et al., "Comparison of the Complete Genome Sequences of *Pseudomonas syringae* pv. *syringae*B728a and pv. *tomato*DC3000", *PNAS*, vol. 102, No. 31, (Aug. 2005), pp. 11064-11069.

Herms, Stefan, et al., "A Strobilurin Fungicide Enhances the Resistance of Tobacco against Tobacco Mosaic Virus and *Pseudomonasx syringae*pv tabaci", *Plant Physiology*, (Sep. 2002), vol. 130, pp. 120-127.

Trumpower, Bernard, "Cytochrome $bc_1$ Complexes of Microorganisms", *Microbiological Reviews*, (Jun. 1990), vol. 54, No. 2, pp. 101-129.

Yeomans, J.C., et al., "Denitrification in Soil: Effects of Insecticides and Fungicides", *Soil Biol. Biochem.*, (1985), vol. 17, No. 4, pp. 453-456.

Extended European Search Report dated Aug. 8, 2013 for Application No. 10751957.1.

* cited by examiner

METHOD FOR REDUCING NITROUS OXIDE EMISSION FROM SOILS

This application is a National Stage application of International Application No. PCT/EP2010/063358 filed Sep. 13, 2010, the entire contents of which is hereby incorporated herein by reference. This application also claims priority under 35 U.S.C. §119 to EP Patent Application No. 09170414.8, filed Sep. 16, 2009, the entire contents of which is hereby incorporated herein by reference.

DESCRIPTION

The present invention relates to a method for reducing nitrous oxide emission from soils comprising treating a plant growing on the respective soil and/or the locus where the plant is growing or is intended to grow and/or the seeds from which the plant grows with at least one fungicide (compound A) selected from the group consisting of:

(A1) inhibitors of complex III at Qo site (respiration inhibitors e.g. strobilurins): azoxystrobin, coumethoxystrobin, coumoxystrobin, dimoxystrobin, enestroburin, fenaminstrobin, fenoxystrobin (flufenoxystrobin), fluoxastrobin, kresoxim-methyl, metominostrobin, orysastrobin, picoxystrobin, pyraclostrobin, pyrametostrobin, pyraoxystrobin, pyribencarb, triclopyricarb (chlorodincarb), trifloxystrobin, 2-[2-(2,5-dimethyl-phenoxymethyl)-phenyl]-3-methoxy-acrylic acid methyl ester and 2-(2-(3-(2,6-di-chlorophenyl)-1-methyl-allylidene-aminooxy-methyl)-phenyl)-2-methoxyimino-N-methyl-acetamide;

(A2) inhibitors of complex III at Qi site (respiration inhibitors): cyazofamid, amisulbrom;

(A3) inhibitors of complex II (respiration inhibitors e.g. carboxanilides): benodanil, bixafen, boscalid, carboxin, fenfuram, fenhexamid, flutolanil, fluxapyroxad, furametpyr, isopyrazam, mepronil, oxycarboxin, penflufen, penthiopyrad, sedaxane, tecloftalam, thifluzamide, N-(4'-trifluoromethylthiobiphenyl-2-yl)-3-difluoromethyl-1-methyl-1H-pyr-azole-4-carboxamide and N-(2-(1,3,3-trimethyl-butyl)-phenyl)-1,3-dimethyl-5-fluoro-1H-pyrazole-4-carboxamide;

(A4) other respiration inhibitors (e.g. complex I inhibitors, uncouplers): diflumetorim; nitrophenyl derivates: binapacryl, dinobuton, dinocap, fluazinam, nitrthalisopropyl, tecnazen, ferimzone; organometal compounds: fentin salts: fentin-acetate, fentin chloride, fentin hydroxide; ametoctradin, silthiofam;

(A5) sterol biosynthesis inhibitors (SBI fungicides):
C14 demethylase inhibitors (DMI fungicides): triazoles: azaconazole, bitertanol, bromuconazole, cyproconazole, difenoconazole, diniconazole, diniconazole-M, epoxiconazole, fenbuconazole, fluopyram, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole; imidazoles: cyazofamid, imazalil, pefurazoate, prochloraz, triflumizol; pyrimidines, pyridines and piperazines: fenarimol, nuarimol, pyrifenox and triforine;
delta14-reductase inhibitors: aldimorph, dodemorph, dodemorph-acetate, fenpropimorph, tridemorph, fenpropidin, piperalin and spiroxamine;
inhibitors of 3-keto reductase: fenhexamid;

(A6) nucleic acid synthesis inhibitors:
phenylamides or acyl amino acid fungicides: benalaxyl, benalaxyl-M, kiralaxyl, metalaxyl, metalaxyl-M (mefenoxam), ofurace, oxadixyl;
others: hymexazole, octhilinone, oxolinic acid, bupirimate;

(A7) inhibitors of cell division and cytoskeleton:
tubulin inhibitors: benzimidazoles, thiophanates: carbendazim, fuberidazole, thiabendazole, thiophanate-methyl; triazolopyrimidines: 5-chloro-7-(4-methyl-piperidin-1-yl)-6-(2,4,6-trifluorophenyl)-[1,2,4]triazolo[1,5-a]pyrimidine
other cell division inhibitors: diethofencarb, ethaboxam, pencycuron, fluopicolide, zoxamide, metrafenone, pyriofenone;

(A8) inhibitors of amino acid and protein synthesis:
methionine synthesis inhibitors (anilino-pyrimidines): cyprodinil, mepanipyrim, nitrapyrin, pyrimethanil;
protein synthesis inhibitors: blasticidin-S, kasugamycin, kasugamycin hydrochloride-hydrate, mildiomycin, streptomycin, oxytetracyclin, polyoxine, validamycin A;

(A9) signal transduction inhibitors:
MAP/histidine kinase inhibitors: fluoroimid, procymidone, vinclozolin, fenpiclonil, fludioxonil;
G protein inhibitors: quinoxyfen;

(A10) lipid and membrane synthesis inhibitors:
phospholipid biosynthesis inhibitors: edifenphos, iprobenfos, pyrazophos, isoprothiolane; cinnamic or mandelic acid amides;
lipid peroxidation: dicloran, quintozene, tecnazene, tolclofos-methyl, biphenyl, chloroneb, etridiazole;
phospholipid biosynthesis and cell wall deposition: dimethomorph, flumorph, mandiproamid, pyrimorph, benthiavalicarb, iprovalicarb, pyribencarb, valifenalate, N-(1-(1-(4-cyano-phenyl)-ethanesulfonyl)-but-2-yl) carbamic acid-(4-fluorophenyl)ester;
compounds affecting cell membrane permeability and fatty acides: propamocarb, propamo-carb-hydrochlorid;

(A11) inhibitors with multi-site action:
inorganic active substances: Bordeaux mixture, copper acetate, copper hydroxide, copper oxychloride, basic copper sulfate, sulfur;
thio- and dithiocarbamates: ferbam, metam, methasulphocarb, metiram, propineb, thiram, zineb, ziram;
organochlorine compounds (e.g. phthalimides, sulfamides, chloronitriles): anilazine, captafol, folpet, dichlofluanid, dichlorophen, flusulfamide, hexachlorobenzene, pentachlorphenole and its salts, phthalide, tolylfluanid, N-(4-chloro-2-nitro-phenyl)-N-ethyl-4-methyl-benzenesulfonamide;
guanidines and others: guanidine, dodine, dodine free base, guazatine, guazatine-acetate, iminoctadine, iminoctadine-triacetate, iminoctadine-tris(albesilate), dithianon;

(A12) cell wall synthesis inhibitors:
inhibitors of glucan synthesis: validamycin, polyoxin B;
melanin synthesis inhibitors: pyroquilon, tricyclazole, carpropamid, dicyclomet, fenoxanil;

(A13) plant defence inducers:
acibenzolar-5-methyl, probenazole, isotianil, tiadinil, phosphonates: fosetyl, fosetyl-aluminum, phosphorous acid and its salts;

(A14) unknown mode of action:
bronopol, chinomethionat, cyflufenamid, cymoxanil, dazomet, debacarb, diclomezine, difenzoquat, difenzoquat-methylsulfate, diphenylamin, fenpyrazamine, flumetover, flusulfamide, flutianil, methasulfocarb, oxincopper, proquinazid, tebufloquin, tecloftalam, triazoxide, 2-butoxy-6-iodo-3-propylchromen-4-one, N-(cyclo-propylmethoxyimino-(6-difluoro-methoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N-methyl formamidine, N'-(4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethyl-silanyl-prop-oxy)-phenyl)-N-ethyl-N-methyl formamidine, N'-(5-difluoromethyl-2-methyl-4-(3-tri-methylsilanyl-propoxy)-phenyl)-N-ethyl-N-methyl formamidine, 2-{1-[2-(5-methyl-3-trifluoromethyl-pyrazole-1-yl)-acetyl]-piperidin-4-yl}-thiazole-4-carboxylic acid methyl-(1,2,3,4-tetrahydro-naphthalen-1-yl)-amide, 2-{1-[2-(5-meth-yl-3-trifluoromethyl-pyrazole-1-yl)-acetyl]-piperidin-4-yl}-thiazole-4-carboxylic acid methyl-(R)-1,2,3,4-tetrahydro-naphthalen-1-yl-amide, methoxy-acetic acid 6-tert-butyl-8-fluoro-2,3-dimethyl-quinolin-4-yl ester and N-Methyl-2-{1-[(5-methyl-3-trifluoro-methyl-1H-pyrazol-1-yl)-acetyl]-piperidin-4-yl}-N-[(1R)-1,2,3,4-tetrahydro-naphthalen-1-yl]-4-thi-azolecarboxamide, 3-[5-(4-chloro-phenyl)-2,3-dimethyl-isoxazolidin-3-yl]-pyridine, 3-[5-(4-methyl-phenyl)-2,3-dimethyl-isoxazolidin-3-yl]-pyridine (pyrisoxazole), N-(6-methoxy-pyridin-3-yl) cyclopropanecarboxylic acid amide, 5-chloro-1-(4,6-dimethoxy-pyrimidin-2-yl)-2-methyl-1H-benzoimidazole, 2-(4-chloro-phenyl)-N-[4-(3,4-dimeth-oxy-phenyl)-isoxazol-5-yl]-2-prop-2-ynyloxy-acetamide;

and at least one ammonium- or urea-containing fertilizer (compound B) selected from the group consisting of:

(B1) inorganic fertilizer:
NPK fertilizer, ammonium nitrate, calcium ammonium nitrate, ammonium sulfate nitrate, ammonium sulfate and ammonium phosphate;

(B2) organic fertilizer:
liquid manure, semi-liquid manure, stable manure and straw manure, worm castings, compost, seaweed and guano;

wherein the application of at least one compound (A) and at least one compound (B) is carried out with a time lag of at least 1 day.

In addition, the present invention relates to a method for reducing nitrous oxide emission from soils as described above, wherein the ammonium- or urea-containing fertilizer (compound B) is applied together with at least one nitrification inhibitor (compound C) selected from the group consisting of 2-(3,4-dimethyl-pyrazol-1-yl)-succinic acid, 3,4-dimethylpyrazolephosphate (DMPP), dicyandiamide (DCD), 1H-1,2,4-triazole, 3-methylpyrazole (3-MP), 2-chloro-6-(trichloromethyl)-pyridine, 5-ethoxy-3-trichloromethyl-1,2,4-thiadiazol, 2-amino-4-chloro-6-methyl-pyrimidine, 2-mercapto-benzothiazole, 2-sulfanilamidothiazole, thiourea, sodium azide, potassium azide, 1-hydroxypyrazole, 2-methylpyrazole-1-carboxamide, 4-amino-1,2,4-triazole, 3-mercapto-1,2,4-triazole, 2,4-diamino-6-trichloromethyl-5-triazine, carbon bisulfide, ammonium thiosulfate, sodium trithiocarbonate, 2,3-dihydro-2,2-dimethyl-7-benzofuranol methyl carbamate and N-(2,6-dimethylphenyl)-N-(methoxy-acetyl)-alanine methyl ester.

Nitrogen is an essential element for plant growth and reproduction. About 25% of the plant-available nitrogen in soils (ammonium and nitrate) originate from decomposition processes (mineralization) of organic nitrogen compounds such as humus, plant and animal residues and organic fertilizers. Approximately 5% derive from rainfall. On a global basis, the biggest part (70%), however, are supplied to the plant by inorganic nitrogen fertilizers. Without the use of nitrogenous fertilizers, the earth would not be able to support its current population.

Soil microorganisms convert organic nitrogen to ammonium ($NH_4^+$) which is subsequently oxidized to nitrate ($NO_3^-$) in a process known as nitrification. Nitrate is very important in agriculture, because it is one form of nitrogen which is preferably taken up by the plants due to its high plant-availability. However, nitrate is also highly mobile in the soil. As a consequence, it may be readily lost from soils leaching to groundwater. In addition, nitrogen is lost by denitrification which is the microbiological conversion of nitrate and nitrite ($NO_2^-$) to gaseous forms of nitrogen such as nitrous oxide ($N_2O$) and molecular nitrogen ($N_2$). As a result of the various losses, approximately 50% of the applied nitrogen is lost during the year following fertilizer addition (cf. Nelson and Huber; Nitrification inhibitors for corn production (2001). National Corn Handbook, Iowa State University).

Consequently, there is great concern that the intensive use of fertilizer and the application of livestock wastes may lead to increased nitrogen levels in the groundwater and surface waters which in turn could lead to increased eutrophication of lakes and streams.

In addition, nitrogen fertilization and livestock wastes may increase the production of nitrous oxide, significantly contributing to the stratospheric ozone destruction and global warming. Besides nitrous oxide, carbon dioxide ($CO_2$) and methane ($CH_4$) are important gases produced by native and agricultural soils. Depending on various parameters such as weather and soil type, increased fertilization and tillage can additionally increase nitrous oxide emissions.

As a consequence, one of the biggest challenge to the world community in the coming years will be the reduction of gases responsible for the greenhouse effect in the atmosphere or at least the stabilization of greenhouse gas concentrations in the atmosphere at a level that would prevent dangerous anthropogenic interference with the climate system. This concern is expressed in the Kyoto Protocol in which the ratifying countries commit to reduce their emissions of greenhouse gases or engage in emissions trading if they maintain or increase emissions of these gases.

One of the best known greenhouse gases is carbon dioxide. However, nitrous oxide is another cause of great concern. Throughout the 20th century and continuing into the 21st century, nitrous oxide has increased by 50 parts per billion in the atmosphere and is rising further by 0.25% each year. Although nitrous oxide only accounts for around 9% of the total greenhouse gas emissions, one has to keep in mind that it has a 300-fold greater global warming potential than carbon dioxide over the next 100 years and an atmospheric lifetime of approximately 150 years.

The above listed trends may result in increased levels of nitrogen in natural waters, crop residue, and municipal and agricultural wastes, creating national and international concerns about the environment and the public health.

Dharnaraj P. S. in Lal and Lal (Editors) (Effects of pesticides on nitrification and denitrification (1988). Pesticides and Nitrogen Cycle) describes the effect of various pesticides on nitrification and denitrification. The studies described therein show that most fungicides do not have any effect on nitrification and denitrification. In addition, the method steps according to the invention as well as the surprising effect are not disclosed.

Mosier et al. (Nitrous oxide emission from agricultural fields; Assessment, measurement and mitigation (1996). Plant and Soil 131: 95.108) summarized the effects of nitrification inhibitors on $N_2O$ emissions from fertilized soils. A number of studies indicated that nitrification inhibitors did limit $N_2O$ emission from soils fertilized with ammonium-based fertilizers.

Furthermore, Kinney et al. (Effects of fungicides on trace gas fluxes (2004). Journal of Geophysical Research 109: 1-15) have hypothesized that the variations in gases flux from agricultural soils may also be affected by the quantity and type of agricultural chemicals (pesticides) used. They carried out field experiments and determined the effect to two commonly used multi-site fungicides, mancozeb and chlorothalonil, on trace gas exchange.

Kinney et al. (Laboratory investigations into the effects of the pesticides mancozeb, chlorothalonil, and prosulfuron on nitrous oxide and nitric oxide production in fertilized soil (2005). Soil Biology & Biochemistry 37: 837-850) additionally investigated the effects of mancozeb, chlorthalonil and the herbicide prosulfuron on $N_2O$ production by nitrifying and denitrifying bacteria in fertilized soil.

Somda et al. (1991). Influence of biocides on tomato nitrogen uptake and soil nitrification and denitirification. Journal of Plant Nutrition 14 (11): 1187-99) investigated the impact of benlate, captan, and lime-sulfur fungicides compared to nitrification inhibitors on nitrification.

WO 98/05607 is directed to the use of inorganic or organic polyacids for the treatment of inorganic fertilizers, in particular the use of the polyacids as a mixture with at least one nitrification inhibitor for the treatment of inorganic fertilizers.

WO 07/0174163 discloses N-(3',4',5'-trifluorobiphenyl-2-yl)-3-difluoromethyl-1-methyl-1H-pyrazole-4-carboxamide. WO 03/009687 discloses 5-ethyl-6-octyl-[1,2,4]triazolo[1,5-a]pyrimidine-7-ylamine). N'-(4-(4-chloro-3-trifluoromethyl-phenoxy)-2,5-dimethyl-phenyl)-N-ethyl-N-methyl formamidine and N'-(4-(4-fluoro-3-trifluoromethyl-phenoxy)-2,5-dimethyl-phenyl)-N-ethyl-N-methyl formamidine are known from WO 00/46184 while N'-(2-methyl-5-trifluormethyl-4-(3-trimethylsilanyl-propoxy)-phenyl)-N-ethyl-N-methyl formamidine and N'-(5-difluormethyl-2-methyl-4-(3-trimethylsilanyl-propoxy)-phenyl)-N-ethyl-N-methyl formamidine are described in WO 03/93224. They can be prepared in the manner described therein.

WO 08/059,053 relates to a method for increasing the carbon dioxide sequestration from the atmosphere by treating a plant, a part of the plant, the locus where the plant is growing or is intended to grow and/or the plant propagules with certain active ingredients. The invention also relates to the use of the compounds for increasing the dry biomass of a plant.

The further active ingredients as well as their pesticidal action and methods for producing them are generally known. For instance, the commercially available compounds may be found in The Pesticide Manual, 14th Edition, British Crop Protection Council (2006) among other publications.

Nitrification and denitrification are the two main processes by which nitrous oxide is produced in soil environments. It is expected that the yearly application of nitrogen fertilizers and pesticides will more than double over the next 50 years. In addition, the agricultural cropland is expected to increase by $5.5 \times 10^8$ ha hectares by the year 2050 (cf. Tilman et al. (2001): Forecasting agriculturally driven global environmental change. Science. Vol. 292: 281-284). As a consequence, agricultural soils will likely have an ever-increasing influence on the global atmospheric budgets of carbon dioxide, nitrous oxide and methane. With respect to agricultural production systems, it could be shown that fertilization and tillage more than double $N_2O$ emissions from soils.

There is also concern that the intensive use of fertilizer and the application of livestock wastes could lead to increased nitrogen levels in groundwater and surface waters, and that this in turn could lead to increased eutrophication of lakes and streams.

Besides the potential impact on global warming, the production of $N_2O$ reduces the amount of nitrogen available to the plants.

It was therefore an object of the present invention to provide a reliable method which solves the problems outlined above, and which should, in particular, reduce nitrous oxide emission from soils. In particular, from soils which are fertilized.

Surprisingly, we have found that this object is achieved when treating a plant and/or the locus such as the soil where the plant is growing or is intended to grow and/or the seeds from which the plant grows with at least one fungicide (compound A) and at least one ammonium- or urea-containing fertilizer (compound B) wherein it is essential that the application of compound (A) and compound (B) is carried out with a time lag of at least 1 day.

The object of the present invention can also be achieved when treating a plant and/or the locus such as the soil where the plant is growing or is intended to grow and/or the seeds from which the plant grows with an agrochemical mixture, comprising at least two fungicides (compound A) and at least one ammonium- or urea-containing fertilizer (compound B) wherein the application of the mixture comprising at least two compounds (A) and compound (B) must be carried out with a time lag of at least 1 day.

The time gap between the application of a fungicide (or a respective mixture comprising at least two fungicides) (compound A) from the application of a fertilizer (compound B) is the crucial method step because it could be shown that the joint application may have no impact or even results in an increased $N_2O$ emission while only a timely separated application of a fungicide and a fertilizer according to the method of the present invention, results in a strong decrease of $N_2O$ emission. Consequently, the time gap between the application of a fungicide (compound A) and a fertilizer (compound B) is a special technical feature which results in a surprising effect being a new and inventive technical teaching to any person skilled in the art.

The application of active ingredients according to the method of the invention provides significant ecological and economical advantages. From an ecological stand point, the cutback of $N_2O$ emissions significantly reduces the impact of modern agriculture on the environment and its atmosphere as well as on global warming. In addition, losses of nitrogen to the groundwater, risk of eutrophication of lakes and streams are also minimized due to an optimized use of soil nitrogen.

In one embodiment of the method according to the invention, the nitrous oxide emission from soils is reduced by applying a fungicide (compound A) selected from the group (A1) consisting of azoxystrobin, coumethoxystrobin, coumoxystrobin, dimoxystrobin, enestroburin, fenaminstrobin, fenoxystrobin (flufenoxystrobin), fluoxastrobin, kresoxim-methyl, metominostrobin, orysastrobin, picoxystrobin, pyraclostrobin, pyrametostrobin, pyraoxystrobin, pyribencarb, triclopyricarb (chlorodincarb), trifloxystrobin, 2-[2-(2,5-dimethyl-phenoxymethyl)-phenyl]-3-methoxy-acrylic acid methyl ester and 2-(2-(3-(2,6-di-chlorophenyl)-1-methyl-allylidene-aminooxy-methyl)-phenyl)-2-methoxyimino-N-methyl-acetamide;

In a preferred embodiment of the method according to the invention, compound (A) is a strobilurin selected from the group consisting of azoxystrobin, dimoxystrobin, fluoxastrobin, kresoxim-methyl, metominostrobin, orysastrobin, picoxystrobin, pyraclostrobin and trifloxystrobin.

In a preferred embodiment of the method according to the invention, compound (A) is a strobilurin selected from the group consisting of pyraclostrobin, orysastrobin, azoxystrobin, dimoxystrobin, enestroburin, fluoxastrobin, kresoxim-methyl, metominostrobin, picoxystrobin, pyribencarb and trifloxystrobin.

In a preferred embodiment of the method according to the invention, compound (A) is a strobilurin selected from the group consisting of azoxystrobin, pyraclostrobin and trifloxystrobin.

In an especially preferred embodiment of the method according to the invention, compound (A) is pyraclostrobin.

In one embodiment of the method according to the invention, the nitrous oxide emission from soils is reduced by applying a fungicide (compound A) selected from the group (A3) consisting of benodanil, bixafen, boscalid, carboxin, fenfuram, fenhexamid, flutolanil, fluxapyroxad, furametpyr, isopyrazam, mepronil, oxycarboxin, penflufen, penthiopyrad, sedaxane, tecloftalam, thifluzamide, N-(4'-trifluoromethylthiobiphenyl-2-yl)-3-difluoromethyl-1-methyl-1H-pyrazole-4-carboxamide and N-(2-(1,3,3-trimethyl-butyl)-phenyl)-1,3-dimethyl-5-fluoro-1H-pyrazole-4-carboxamide.

In a preferred embodiment of the method according to the invention, compound (A) is a carboxanilide selected from the group consisting of bixafen, boscalid, fluxapyroxad, fluopyram, isopyrazam, penflufen, penthiopyrad and sedaxane.

In another preferred embodiment of the method according to the invention, compound (A) is a carboxanilide selected from the group consisting of bixafen, boscalid, fluxapyroxad, isopyrazam, penflufen, penthiopyrad and sedaxane.

In an especially preferred embodiment of the method according to the invention, compound (A) is a carboxanilides selected from the group consisting of bixafen, boscalid, fluxapyroxad and isopyrazam.

In an especially preferred embodiment of the method according to the invention, compound (A) is boscalid.

In an especially preferred embodiment of the method according to the invention, compound (A) is fluxapyroxad.

In one embodiment of the method according to the invention, the nitrous oxide emission from soils is reduced by applying a fungicide (compound A) selected from the group (A5) consisting of azaconazole, bitertanol, bromuconazole, cyproconazole, difenoconazole, diniconazole, diniconazole-M, epoxiconazole, fenbuconazole, fluopyram, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole, cyazofamid, imazalil, pefurazoate, prochloraz, triflumizol, fenarimol, nuarimol, pyrifenox, triforine, aldimorph, dodemorph, dodemorph-acetate, fenpropimorph, tridemorph, fenpropidin, piperalin, spiroxamine and fenhexamid.

In a preferred embodiment of the method according to the invention, compound (A) is a C14 demethylase inhibitor selected from the group consisting of difenoconazole, epoxiconazole, fluopyram, fluquinconazole, metconazole, prothioconazole, triticonazole and prochloraz.

In an especially preferred embodiment of the method according to the invention, compound (A) is epoxiconazole.

In another especially preferred embodiment of the method according to the invention, compound (A) is metconazole.

In a preferred embodiment of the method according to the invention, compound (A) is a delta14-reductase inhibitor selected from the group consisting of fenpropimorph, tridemorph and fenpropidin.

In an especially preferred embodiment of the method according to the invention, compound (A) is fenpropimorph.

In one embodiment of the method according to the invention, the nitrous oxide emission from soils is reduced by applying a fungicide (compound A) selected from the group (A6) consisting of benalaxyl, benalaxyl-M, kiralaxyl, metalaxyl, metalaxyl-M (mefenoxam), ofurace, oxadixyl, hymexazole, octhilinone, oxolinic acid and bupirimate.

In a preferred embodiment of the method according to the invention, compound (A) is a nucleic acid synthesis inhibitor selected from the group consisting of benalaxyl, benalaxyl-M, metalaxyl and metalaxyl-M (mefenoxam).

In one embodiment of the method according to the invention, the nitrous oxide emission from soils is reduced by applying a fungicide (compound A) selected from the group (A7) consisting of benzimidazoles, thiophanates: carbendazim, fuberidazole, thiabendazole, thiophanate-methyl, 5-chloro-7-(4-methyl-piperidin-1-yl)-6-(2,4,6-trifluorophenyl)-[1,2,4]triazolo[1,5-a]pyrimidine, diethofencarb, ethaboxam, pencycuron, fluopicolide, zoxamide, metrafenone and pyriofenone.

In a preferred embodiment of the method according to the invention, compound (A) is a inhibitor of cell division and cytoskeleton selected from the group consisting of thiophanate-methyl and metrafenone.

In an especially preferred embodiment of the method according to the invention, compound (A) is pyrimethanil.

In one embodiment of the method according to the invention, the nitrous oxide emission from soils is reduced by applying a fungicide (compound A) selected from the group (A10) consisting of edifenphos, iprobenfos, pyrazophos, isoprothiolane, dicloran, quintozene, tecnazene, tolclofos-methyl, biphenyl, chloroneb, etridiazole, dimethomorph, flumorph, mandiproamid, pyrimorph, benthiavalicarb, iprovalicarb, pyribencarb, valifenalate, N-(1-(1-(4-cyanophenyl)-ethanesulfonyl)-but-2-yl)carbamic acid-(4-fluorophenyl)ester, propamocarb and propamocarb-hydrochlorid.

In a preferred embodiment of the method according to the invention, compound (A) is a lipid an membrane synthesis inhibitor selected from the group consisting of dimethomorph and mandiproamid.

In an especially preferred embodiment of the method according to the invention, compound (A) is dimethomorph.

In one embodiment of the method according to the invention, the nitrous oxide emission from soils is reduced by applying a fungicide (compound A) selected from the group (A11) consisting of Bordeaux mixture, copper acetate, copper hydroxide, copper oxychloride, basic copper sulfate, sulfur, ferbam, metam, methasulphocarb, metiram, propineb, thiram, zineb, ziram, anilazine, captafol, folpet, dichlofluanid, dichlorophen, flusulfamide, hexachlorobenzene, pentachlorphenole and its salts, phthalide, tolylfluanid, N-(4-chloro-2-nitro-phenyl)-N-ethyl-4-methyl-benzenesulfonamide, guanidine, dodine, dodine free base, guazatine, guazatine-acetate, iminoctadine, iminoctadine-triacetate, iminoctadine-tris(albesilate) and dithianon.

In a preferred embodiment of the method according to the invention, compound (A) is a metiram.

In another preferred embodiment of the method according to the invention, compound (A) is dithianon.

In one embodiment of the method according to the invention, the nitrous oxide emission from soils is reduced by applying a fungicide (compound A) selected from the group (A14) consisting of bronopol, chinomethionat, cyflufenamid, cymoxanil, dazomet, debacarb, diclomezine, difenzoquat, difenzoquat-methylsulfate, diphenylamin, fenpyrazamine, flumetover, flusulfamide, flutianil, methasulfocarb, oxincopper, proquinazid, tebufloquin, tecloftalam, triazoxide, 2-butoxy-6-iodo-3-propylchromen-4-one, N-(cyclo-propyl-methoxy-imino-(6-difluoro-methoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N-methyl formamidine, N'-(4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethyl-silanyl-propoxy)-phenyl)-N-ethyl-N-methyl formamidine, N'-(5-difluoromethyl-2-methyl-4-(3-tri-methylsilanyl-propoxy)-phenyl)-N-ethyl-N-methyl formamidine, 2-{1-[2-(5-methyl-3-trifluoromethyl-pyrazole-1-yl)-acetyl]-piperidin-4-yl}-thiazole-4-carboxylic acid methyl-(1,2,3,4-tetrahydronaphthalen-1-yl)-amide, 2-{1-[2-(5-meth-yl-3-trifluoromethyl-pyrazole-1-yl)-acetyl]-piperidin-4-yl}-thiazole-4-carboxylic acid methyl-(R)-1,2,3,4-tetrahydronaphthalen-1-yl-amide, methoxy-acetic acid 6-tert-butyl-8-fluoro-2,3-dimethyl-quinolin-4-yl ester and N-Methyl-2-{1-[(5-methyl-3-trifluoro-methyl-1H-pyrazol-1-yl)-acetyl]-piperidin-4-yl}-N-[(1R)-1,2,3,4-tetrahydro-naphthalen-1-yl]-4-thi-azolecarboxamide, 3-[5-(4-chloro-phenyl)-2,3-dimethyl-isoxazolidin-3-yl]-pyridine, 3-[5-(4-methyl-phenyl)-2,3-dimethyl-isoxazolidin-3-yl]-pyridine (pyrisoxazole), N-(6-methoxy-pyridin-3-yl)cyclopropanecarboxylic acid amide, 5-chloro-1-(4,6-dimethoxy-pyrimidin-2-yl)-2-methyl-1H-benzoimidazole and 2-(4-chloro-phenyl)-N-[4-(3,4-dimethoxy-phenyl)-isoxazol-5-yl]-2-prop-2-ynyloxy-acetamide.

In one embodiment of the method according to the invention, compound (B) is an ammonium- or urea-containing fertilizer (compound B) selected from the group of inorganic fertilizer (B1) consisting of NPK fertilizer, ammonium nitrate, calcium ammonium nitrate, ammonium sulfate nitrate, ammonium sulfate and ammonium phosphate.

In a preferred embodiment of the method according to the invention, compound (B) is selected from the group consisting of ammonium sulfate nitrate and ammonium sulfate.

In another embodiment of the method according to the invention, compound (B) is an ammonium- or urea-containing fertilizer (compound B) selected from the group of organic fertilizer (B2) consisting of liquid manure, semiliquid manure, stable manure and straw manure, worm castings, compost, seaweed and guano.

In a preferred embodiment of the method according to the invention, compound (B) is liquid manure.

In one embodiment of the method according to the invention, the application of at least one compound (A) and at least one compound (B) is carried out with a time lag of at least 1 day.

In a preferred embodiment of the method according to the invention, the application of at least one compound (A) and at least one compound (B) is carried out with a time lag of at least 4 days.

In another preferred embodiment of the method according to the invention, the application of at least one compound (A) and at least one compound (B) is carried out with a time lag of at least 8 days.

In another preferred embodiment of the method according to the invention, the application of at least one compound (A) and at least one compound (B) is carried out with a time lag of at least 10 days.

In yet another preferred embodiment of the method according to the invention, the application of at least one compound (A) and at least one compound (B) is carried out with a time lag of at least 16 days.

The remarks as to preferred embodiments of the compounds (A) and (B) and mixtures comprising at least two compounds (A) and mixture comprising at least one compound (B) and at least one compound (C), to their preferred use and methods of using them are to be understood either each on their own or preferably in combination with each other.

In one embodiment of the method according to the invention, the nitrous oxide emission from soils is reduced by applying the ammonium- or urea-containing fertilizer (compound B) together with at least one nitrification inhibitor (compound C) selected from the group consisting of 2-(3,4-dimethyl-pyrazol-1-yl)-succinic acid, 3,4-dimethylpyrazolephosphate (DMPP), dicyandiamide (DCD), 1H-1,2,4-triazole, 3-methylpyrazole (3-MP), 2-chloro-6-(trichloromethyl)-pyridine, 5-ethoxy-3-trichloromethyl-1,2,4-thiadiazol, 2-amino-4-chloro-6-methyl-pyrimidine, 2-mercapto-benzothiazole, 2-sulfanilamidothiazole, thiourea, sodium azide, potassium azide, 1-hydroxypyrazole, 2-methylpyrazole-1-carboxamide, 4-amino-1,2,4-triazole, 3-mercapto-1,2,4-triazole, 2,4-diamino-6-trichloromethyl-5-triazine, carbon bisulfide, ammonium thiosulfate, sodium trithiocarbonate, 2,3-dihydro-2,2-dimethyl-7-benzofuranol methyl carbamate and N-(2,6-dimethylphenyl)-N-(methoxyacetyl)-alanine methyl ester.

In a preferred embodiment of the method according to the invention, the nitrous oxide emission from soils is reduced by applying the ammonium- or urea-containing fertilizer (compound B) together with at least one nitrification inhibitor (compound C) selected from the group consisting of 2-(3,4-dimethyl-pyrazol-1-yl)-succinic acid, 3,4-dimethylpyrazolephosphate (DMPP), dicyandiamide (DCD), 1H-1,2,4-triazole, 3-methylpyrazole (3-MP), 2-chloro-6-(trichloromethyl)-pyridine and 5-ethoxy-3-trichloromethyl-1,2,4-thiadiazol.

In another embodiment of the method according to the invention, the nitrous oxide emission from soils is reduced by applying an agrochemical mixture comprising at least one compound (B) and at least one nitrification inhibitor (compound C).

In another embodiment of the method according to the invention, the nitrous oxide emission from soils is reduced by applying an agrochemical mixture comprising one compound (B) and one nitrification inhibitor (compound C).

The secondary mixtures listed in table 1, comprising one compound (B) and one compound (C) are a preferred embodiment of the method of the current invention.

TABLE 1

| Mixture | Compound (B) | Compound (C) |
| --- | --- | --- |
| T1 | ammonium sulfate nitrate | 3,4-dimethylpyrazolephosphate |
| T2 | ammonium sulfate | 3,4-dimethylpyrazolephosphate |
| T3 | ammonium sulfate nitrate | dicyandiamide |
| T4 | ammonium sulfate | dicyandiamide |
| T5 | ammonium sulfate nitrate | 2-chloro-6-(trichloromethyl)-pyridine |
| T6 | ammonium sulfate | 2-chloro-6-(trichloromethyl)-pyridine |
| T7 | ammonium sulfate nitrate | 2-(3,4-dimethyl-pyrazol-1-yl)-succinic acid |
| T8 | ammonium sulfate | 2-(3,4-dimethyl-pyrazol-1-yl)-succinic acid |

In a preferred embodiment of method according to the invention, the agrochemical mixture comprises two compounds (A) as defined in any embodiment described above.

In another preferred embodiment of method according to the invention, the agrochemical mixture comprises three compounds (A) as defined in any embodiment described above.

In the terms of the present invention "agrochemical mixture" is not restricted to a physical mixture comprising at least two compounds, but refers to any preparation form of at least one compound and at least one further compound, the use of which is time- and locus-related.

In one embodiment of the invention "agrochemical mixture" refers to a physical mixture comprising two compounds (A).

In one embodiment of the invention "agrochemical mixture" refers to a physical mixture of at least one compound (B) and at least one compound (C).

The agrochemical mixtures may be formulated separately but applied in a temporal relationship, i.e. simultaneously or subsequently, the subsequent application having a time interval which allows a combined action of the compounds.

Furthermore, the individual compounds of the agrochemical mixtures according to the invention such as parts of a kit or parts of the binary mixture may be mixed by the user himself in a spray tank and further auxiliaries may be added, if appropriate (tank mix). This applies also in case ternary mixtures are used according to the invention.

In a preferred embodiment two compounds (A) selected from the group consisting of pyraclostrobin, azoxystrobin, trifloxystrobin, epoxiconazole, metconazole, metrafenone, fluxapyroxad, boscalid, bixafen, isopyrazam, penthiopyrad, fluopyram and fenpropimorph are applied within the method of the invention.

With respect to their intended use in the methods of the present invention, the following secondary mixtures listed in table 2, comprising two compounds (A) are a especially preferred embodiment of the present invention.

TABLE 2

| | (A) | (A) |
|---|---|---|
| M-1 | Boscalid | Pyraclostrobin |
| M-2 | Boscalid | Epoxiconazole |
| M-3 | Boscalid | Metconazole |
| M-4 | Boscalid | Metrafenone |
| M-5 | Boscalid | N-(3',4',5'-trifluorobiphenyl-2-yl)-3-difluoromethyl-1-methyl-1H-pyrazole-4-carboxamide (fluxapyroxad) |
| M-6 | Pyraclostrobin | Epoxiconazole |
| M-7 | Pyraclostrobin | Metconazole |
| M-8 | Pyraclostrobin | Metrafenone |
| M-9 | Pyraclostrobin | N-(3',4',5'-trifluorobiphenyl-2-yl)-3-difluoromethyl-1-methyl-1H-pyrazole-4-carboxamide (fluxapyroxad) |
| M-10 | Pyraclostrobin | Bixafen |
| M-11 | Pyraclostrobin | Isopyrazam |
| M-12 | Pyraclostrobin | Prothioconazole |
| M-13 | Pyraclostrobin | Penthiopyrad |
| M-14 | Pyraclostrobin | Fluopyram |
| M-15 | Pyraclostrobin | Azoxystrobin |
| M-16 | Pyraclostrobin | Trifloxystrobin |
| M-17 | Pyraclostrobin | Fenpropimorph |
| M-18 | Fipronil | N-(3',4',5'-trifluorobiphenyl-2-yl)-3-difluoromethyl-1-methyl-1H-pyrazole-4-carboxamide (fluxapyroxad) |
| M-19 | Epoxiconazole | Bixafen |
| M-20 | Epoxiconazole | Isopyrazam |
| M-21 | Epoxiconazole | Penthiopyrad |
| M-22 | Epoxiconazole | Fluoyram |
| M-23 | Epoxiconazole | Azoxystrobin |
| M-24 | Epoxiconazole | Trifloxystrobin |
| M-25 | Epoxiconazole | Fenpropimorph |
| M-26 | Epoxiconazole | N-(3',4',5'-trifluorobiphenyl-2-yl)-3-difluoromethyl-1-methyl-1H-pyrazole-4-carboxamide (fluxapyroxad) |

Within the mixtures of table 2, the following mixtures are especially preferred: M-1, M-2, M-3, M-6, M-7, M-9, M-17, M-20, M-23, M-25, M-24 and M-26. Within this subset, the following mixtures are preferred: M-1, M-2, M-3, M-6, M-7, M-9, M-23, M-25 and M-26. The following mixtures are more preferred: M-1, M-2, M-3, M-6, M-7, M-9 and M-26. The following mixtures are most preferred: M-1, M-2, M-6, M-9, and M-26. Utmost preference is given to mixture M1.

Consequently, utmost preference is given to the agrochemical mixture comprising pyraclostrobin and boscalid as compounds (A).

All mixtures set forth above are also an embodiment of the present invention.

In one embodiment of the method according to the present invention, ternary mixtures may be applied comprising three compounds (A).

In one embodiment of the method according to the present invention, ternary mixtures may be applied comprising one compound (B) and two compounds (C).

In another embodiment of the method according to the present invention, ternary mixtures may be applied comprising two compounds (B), and one compound (C).

In one embodiment of the invention, the method according to the invention comprises the steps a) application of at least one compound (A) as defined in any of the embodiments above; and b) application of at least one compound (B) as defined in any of the embodiments above; to a plant and/or the locus where the plant is growing or is intended to grow and/or the seeds from which the plant grows, wherein the application of at least one compound (A) in step a) and at least one compound (B) in step b) is carried out with a time lag of at least 1 day.

In another embodiment of the invention, the method according to the invention comprises the steps a) application of at least one compound (A) as defined in any of the embodiments above; and b) application of at least one compound (B) as defined in any of the embodiments above together with at least one compound (C) as defined in any of the embodiments above; to a plant and/or the locus where the plant is growing or is intended to grow and/or the seeds from which the plant grows wherein the application of at least one compound (A) in step a) and at least one compound (B) together with at least one compound (C) in step b) is carried out with a time lag of at least 1 day.

In yet another embodiment of the invention, the method according to the invention comprises the steps a) application of at least one compound (B) as defined in any of the embodiments above; and b) application of at least one compound (A) as defined in any of the embodiments above; to a plant and/or the locus where the plant is growing or is intended to grow and/or the seeds from which the plant grows, wherein the application of at least one compound (B) in step a) and at least one compound (a) in step b) is carried out with a time lag of at least 1 day.

In yet another embodiment of the invention, the method according to the invention comprises the steps a) application of at least one compound (B) as defined in any of the embodiments above together with at least one compound (C) as defined in any of the embodiments above; and b) application of at least one compound (A) as defined in any of the embodiments above to a plant and/or the locus where the plant is growing or is intended to grow and/or the seeds from which the plant grows; wherein the application of at least one compound (B) together with at least one compound (C) in step a) and the application of at least one compound (A) in step b) is carried out with a time lag of at least 1 day.

The plants to be treated according to the invention are selected from the group consisting of agricultural, silvicultural, ornamental and horticultural plants, each in its natural or genetically modified form, more preferably from agricultural plants.

More preferred agricultural plants are field crops, such as potatoes, sugar beets, wheat, barley, rye, oat, sorghum, rice, corn, cotton, rape, oilseed rape, canola, soybeans, peas, field beans, sunflowers, sugar cane; cucumbers, tomatoes, onions, leeks, lettuce, squashes; even more preferably the plant is selected from the group consisting of wheat, barley, oat, rye, soybean, corn, oilseed rape, cotton, sugar cane, rice and sorghum.

In an especially preferred embodiment of the current invention, the plants to be treated are selected from the group consisting of wheat, barley, oat, rye, soybean, corn, oilseed rape, canola, sunflower, cotton, sugar cane, sugar beet, rice and sorghum.

In one embodiment, the aforementioned method for reducing nitrous oxide emission from soils comprises treating the plant propagules, preferably the seeds of an agricultural, horticultural, ornamental or silvicultural plant selected from the group consisting of transgenic or non-transgenic plants.

The term "plants" is to be understood as plants of economic importance and/or men-grown plants. They are preferably selected from agricultural, silvicultural and horticultural (including ornamental) plants. The term "plant" as used herein includes all parts of a plant such as germinating seeds, emerging seedlings, herbaceous vegetation as well as established woody plants including all belowground portions (such as the roots) and aboveground portions.

The term "nitrification inhibitors" is to be understood as any chemical substance which slows down or stops the nitrification process. Nitrification inhibitors retard the natural transformation of ammonium into nitrate, by inhibiting the activity of bacteria such as *Nitrosomonas* spp.

The term "nitrification" is to be understood as the biological oxidation of ammonia ($NH_3$) or ammonium ($NH_4^+$) with oxygen into nitrite ($NO_2^-$) followed by the oxidation of these nitrites into nitrates ($NO_3^-$) by microorganisms. Besides nitrate ($NO_3^-$) nitrous oxide is also produced though nitrification. Nitrification is an important step in the nitrogen cycle in soil.

The term "denitrification" is to be understood as the microbiological conversion of nitrate ($NO_3^-$) and nitrite ($NO_2^-$) to gaseous forms of nitrogen, generally $N_2$ or $N_2O$. This respiratory process reduces oxidized forms of nitrogen in response to the oxidation of an electron donor such as organic matter. The preferred nitrogen electron acceptors in order of most to least thermodynamically favorable include: nitrate ($NO^{3-}$), nitrite ($NO^{2-}$), nitric oxide (NO), and nitrous oxide ($N_2O$). Within the general nitrogen cycle, denitrification completes the cycle by returning $N_2$ to the atmosphere. The process is performed primarily by heterotrophic bacteria (such as *Paracoccus denitrificans* and various pseudomonads), although autotrophic denitrifiers have also been identified (e.g. *Thiobacillus denitrificans*). Denitrifiers are represented in all main phylogenetic groups. When faced with a shortage of oxygen many bacterial species, are able switch from using oxygen to using nitrates to support respiration in a process known as denitrification, during which the water-soluble nitrates are converted to gaseous products, including nitrous oxide, that are emitted into the atmosphere.

"Nitrous oxide", commonly known as happy gas or laughing gas, is a chemical compound with the chemical formula $N_2O$. At room temperature, it is a colorless non-flammable gas. Nitrous oxide is produced naturally in soils through the microbial processes of nitrification and denitrification. These natural emissions of nitrous oxide can be increased by a variety of agricultural practices and activities including for example a) direct addition of nitrogen to soils by using mineral and organic fertilizers b) growing of nitrogen-fixing crops c) cultivation of high organic content soils d) application of livestock manure to croplands and pasture.

The term "fertilizers" is to be understood as chemical compounds applied to promote plant and fruit growth. Fertilizers are typically applied either through the soil (for uptake by plant roots) or by foliar feeding (for uptake through leaves). The term "fertilizers" can be subdivided into two major categories: a) organic fertilizers (composed of decayed plant/animal matter) and b) inorganic fertilizers (composed of chemicals and minerals). Organic fertilizers include manure, slurry, worm castings, peat, seaweed, sewage, and guano. Green manure crops are also regularly grown to add nutrients (especially nitrogen) to the soil. Manufactured organic fertilizers include compost, blood meal, bone meal and seaweed extracts. Further examples are enzyme digested proteins, fish meal, and feather meal. The decomposing crop residue from prior years is another source of fertility. In addition, naturally occurring minerals such as mine rock phosphate, sulfate of potash and limestone are also considered inorganic fertilizers. Inorganic fertilizers are usually manufactured through chemical processes (such as the Haber process), also using naturally occurring deposits, while chemically altering them (e.g. concentrated triple superphosphate). Naturally occurring inorganic fertilizers include Chilean sodium nitrate, mine rock phosphate, and limestone.

"NPK fertilizer" are inorganic fertilizers formulated in appropriate concentrations and combinations comprising the three main nutrients nitrogen (N), phosphorus (P) and potassium (K).

In one embodiment, the plant to be treated according to the method of the invention is an agricultural plant. "Agricultural plants" are plants of which a part (e.g. seeds) or all is harvested or cultivated on a commercial scale or which serve as an important source of feed, food, fibres (e.g. cotton, linen), combustibles (e.g. wood, bioethanol, biodiesel, biomass) or other chemical compounds. Preferred agricultural plants are for example cereals, e.g. wheat, rye, barley, triticale, oats, sorghum or rice, beet, e.g. sugar beet or fodder beet; fruits, such as pomes, stone fruits or soft fruits, e.g. apples, pears, plums, peaches, almonds, cherries, strawberries, raspberries, blackberries or gooseberries; leguminous plants, such as lentils, peas, alfalfa or soybeans; oil plants, such as rape, oil-seed rape, canola, linseed, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, canola, sugar cane or oil palm; tobacco; nuts; coffee; tea; bananas; vines (table grapes and grape juice grape vines); hop; turf; natural rubber plants.

In one embodiment, the plant to be treated according to the method of the invention is a horticultural plant. The term "horticultural plants" are to be understood as plants which are commonly used in horticulture—e.g. the cultivation of ornamentals, vegetables and/or fruits. Examples for ornamentals are turf, geranium, pelargonia, petunia, begonia and fuchsia. Examples for vegetables are potatoes, tomatoes, peppers, cucurbits, cucumbers, melons, watermelons, garlic, onions, carrots, cabbage, beans, peas and lettuce and more preferably from tomatoes, onions, peas and lettuce. Examples for fruits are apples, pears, cherries, strawberry, citrus, peaches, apricots and blueberries.

In one embodiment, the plant to be treated according to the method of the invention is an ornamental plants. "Ornamental plants" are plants which are commonly used in gardening, e.g. in parks, gardens and on balconies. Examples are turf, geranium, pelargonia, petunia, begonia and fuchsia.

In one embodiment, the plant to be treated according to the method of the invention is a silvicultural plants. The term "silvicultural plant" is to be understood as trees, more specifically trees used in reforestation or industrial plantations. Industrial plantations generally serve for the commercial production of forest products, such as wood, pulp, paper, rubber tree, Christmas trees, or young trees for gardening purposes. Examples for silvicultural plants are conifers, like pines, in particular *Pinus* spec., fir and spruce, eucalyptus, tropical trees like teak, rubber tree, oil palm, willow (*Salix*), in particular *Salix* spec., poplar (cottonwood), in particular *Populus* spec., beech, in particular *Fagus* spec., birch, oil palm, and oak.

The term "locus" is to be understood as any type of environment, soil, area or material where the plant is growing or intended to grow. Especially preferred according to the invention is soil.

In the terms of the present invention "mixture" or "agrochemical mixture" means a combination of at least two compounds.

The term "at least one" is to be understood as 1, 2, 3 or more of the respective compound selected from the group consisting of fungicides (compound A), fertilizer (compound B) and nitrification inhibitors (compound C).

The term "genetically modified plants" is to be understood as plants, which genetic material has been modified by the use of recombinant DNA techniques in a way that under natural circumstances it cannot readily be obtained by cross breeding, mutations or natural recombination.

The term "plant propagation material" is to be understood to denote all the generative parts of the plant such as seeds and vegetative plant material such as cuttings and tubers (e.g. potatoes), which can be used for the multiplication of the plant. This includes seeds, grains, roots, fruits, tubers, bulbs, rhizomes, cuttings, spores, offshoots, shoots, sprouts and other parts of plants, including seedlings and young plants, which are to be transplanted after germination or after emergence from soil, meristem tissues, single and multiple plant cells and any other plant tissue from which a complete plant can be obtained.

The term "propagules" or "plant propagules" is to be understood to denote any structure with the capacity to give rise to a new plant, e.g. a seed, a spore, or a part of the vegetative body capable of independent growth if detached from the parent. In a preferred embodiment, the term "propagules" or "plant propagules" denotes for seed.

The reduction of nitrous oxide emission is independent of the presence of pests. Accordingly, in a preferred embodiment of the method, the application of the active ingredients (compound A) and/or mixtures comprising at least one compound (A) is carried out in the absence of pest pressure.

The term "BBCH principal growth stage" refers to the extended BBCH-scale which is a system for a uniform coding of phenologically similar growth stages of all mono- and dicotyledonous plant species in which the entire developmental cycle of the plants is subdivided into clearly recognizable and distinguishable longer-lasting developmental phases. The BBCH-scale uses a decimal code system, which is divided into principal and secondary growth stages. The abbreviation BBCH derives from the Federal Biological Research Centre for Agriculture and Forestry (Germany), the Bundessortenamt (Germany) and the chemical industry.

In one embodiment of the invention, at least one compound (A) is applied at a growth stage (GS) between GS 00 and GS 65 BBCH of the plant.

In preferred embodiment of the invention, at least one compound (A) is applied at a growth stage between GS 14 and GS 55 BBCH of the plant.

In a more preferred embodiment of the invention, at least one compound (A) is applied at the growth stage between GS 14 and GS 47 BBCH of the plant.

In one embodiment of the invention, at least one fertilizer (compound B) is applied before and at sowing, before emergence, and until harvest (GS 00 to GS 89 BBCH).

In another embodiment of the invention, at least one fertilizer (compound B) is applied together with at least one nitrification inhibitor (compound C) before and at sowing, before emergence, and until harvest (GS 00 to GS 89 BBCH).

In another embodiment of the invention, at least one compound (A) is applied during leaf development to flowering (GS 14 to GS 65 BBCH) of the treated plant, provided that the application of at least one compound (A) and at least one compound (B) is carried out with a time lag of at least 1 day.

In a preferred embodiment of the invention, an agrochemical mixture comprising an ammonium- or urea-containing fertilizer (compound B) and at least one nitrification inhibitor (compound C) is applied at least once during the growth stages GS 00 to GS 89 BBCH (before sowing until harvest) while at least one compound (A) is applied at least once during the growth stages GS 14 to GS 65 BBCH (leaf development to flowering) of the treated plant, provided that the application of at least one compound (A) and at least one compound (B) is carried out with a time lag of at least 1 day.

In another embodiment of the invention, the agrochemical mixture comprising an ammonium- or urea-containing fertilizer (compound B) and at least one nitrification inhibitor (compound C) is applied before and at sowing, before emergence, and until shooting/shoot development (GS 00 to GS 33 BBCH) of the plant while at least one compound (A) is applied during leaf development to inflorescence emergence (GS 14 to GS 55 BBCH) provided that the application of at least one compound (A) and at least one compound (B) is carried out with a time lag of at least 1 day.

If an agricultural mixture comprising at least two compounds (A) according to the present invention is used in this inventive method, the plant propagules are preferably treated simultaneously (together or separately) or subsequently.

The subsequent application is carried out with a time interval which allows a combined action of the applied compounds. Preferably, the time interval for a subsequent application of a first compound (A) and a second compound (A) ranges from a few seconds up to 3 months, preferably, from a few seconds up to 1 month, more preferably from a few seconds up to 2 weeks, even more preferably from a few seconds up to 3 days and in particular from 1 second up to 24 hours.

In a preferred embodiment of the invention, the application according to the method of the current invention is repeatedly carried out. In one embodiment, the application is repeated two to ten times, preferably, two to five times; most preferably two times.

In one embodiment, the application of at least one compound (A) is repeatedly carried out. In another embodiment, the application of at least one compound (B) is repeatedly carried out. In yet another embodiment, the application of one compound (B) together with one compound (C) is repeatedly applied. In each case, there must be a time lag of at least 1 day between the last application of at least one compound (A) and the last application of at least one compound (B) (optionally together with at least one compound C).

For the use according to the invention, the application rates of compounds (A) are between 0.01 g and 5 kg of active ingredient per hectare, preferably between 1 g and 1 kg of active ingredient per hectare, especially preferred between 50 g and 300 g of active ingredient per hectare depending on different parameters such as the specific active ingredient applied and the plant species treated.

In the treatment of seed, amounts of from 0.001 g to 20 g per kg of seed, preferably from 0.01 g to 10 g per kg of seed, more preferably from 0.05 to 2 g per kg of seed of compound (A) are generally required.

As a matter of course, compounds (A), (B) and (C) and in case mixtures are employed, compounds selected from the group consisting of compounds (A), (B) and (C) are used in an effective and non-phytotoxic amount. This means that they are used in a quantity which allows to obtain the desired effect but which does not give rise to any phytotoxic symptoms on the treated plant or on the plant raised from the treated propagule or treated soil.

In the methods according to the invention, the application rates of the mixtures comprising at least two compounds (A) are from 0.3 g/ha to 5000 g/ha, preferably 5 g/ha to 2000 g/ha, more preferably from 20 to 1000 g/ha, in particular from 20 to 500 g/ha, depending on the type of compound and the desired effect.

In the treatment of plant propagules, preferably seed, application rates of mixture of the present invention comprising at least two compounds (A) are generally from 0.001 to 1000 g per 100 kg, preferably from 0.01 to 500 g per 100 kg, in particular from 0.1 g to 250 g per 100 kg of plant propagules.

For the use according to the invention, the application rates of compounds (B) are between 10 kg and 300 kg of N per hectare, preferably between 50 kg and 250 kg of N per hectare.

In all embodiments, the agrochemical mixtures are applied in nitrous oxide emission from soils reducing amounts. In one embodiment, the agrochemical mixtures are applied in synergistically the nitrous oxide emission from soils reducing amounts.

The compounds according to the invention can be present in different crystal modifications whose biological activity may differ. They are likewise subject matter of the present invention.

In an especially preferred embodiment of the method according to the invention, compound (A) is applied as seed treatment.

In another especially preferred embodiment of the method according to the invention, compound (A) is applied as foliar and/or in-furrow application.

The compounds according to the invention, their N-oxides and salts can be converted into customary types of agrochemical compositions, e.g. solutions, emulsions, suspensions, dusts, powders, pastes and granules. The composition type depends on the particular intended purpose; in each case, it should ensure a fine and uniform distribution of the compound according to the invention.

Examples for composition types are suspensions (SC, OD, FS), emulsifiable concentrates (EC), emulsions (EW, EO, ES), microemulsions (ME), pastes, pastilles, wettable powders or dusts (WP, SP, SS, WS, DP, DS) or granules (GR, FG, GG, MG), which can be water-soluble or wettable, as well as gel formulations for the treatment of plant propagation materials such as seeds (GF). Usually the composition types (e.g. SC, OD, FS, EC, WG, SG, WP, SP, SS, WS, GF) are employed diluted. Composition types such as DP, DS, GR, FG, GG and MG are usually used undiluted.

The compositions are prepared in a known manner (cf. U.S. Pat. No. 3,060,084, EP-A 707 445 (for liquid concentrates), Browning: "Agglomeration", Chemical Engineering, Dec. 4, 1967, 147-48, Perry's Chemical Engineer's Handbook, 4th Ed., McGraw-Hill, New York, 1963, S. 8-57 and ff. WO 91/13546, U.S. Pat. No. 4,172,714, U.S. Pat. No. 4,144,050, U.S. Pat. No. 3,920,442, U.S. Pat. No. 5,180,587, U.S. Pat. No. 5,232,701, U.S. Pat. No. 5,208,030, GB 2,095,558, U.S. Pat. No. 3,299,566, Klingman: Weed Control as a Science (J. Wiley & Sons, New York, 1961), Hance et al.: Weed Control Handbook (8th Ed., Blackwell Scientific, Oxford, 1989) and Mollet, H. and Grubemann, A.: Formulation technology (Wiley VCH Verlag, Weinheim, 2001).

The agrochemical compositions may also comprise auxiliaries which are customary in agrochemical compositions. The auxiliaries used depend on the particular application form and active substance, respectively. Examples for suitable auxiliaries are solvents, solid carriers, dispersants or emulsifiers (such as further solubilizers, protective colloids, surfactants and adhesion agents), organic and anorganic thickeners, bactericides, anti-freezing agents, anti-foaming agents, if appropriate colorants and tackifiers or binders (e.g. for seed treatment formulations).

Suitable solvents are water, organic solvents such as mineral oil fractions of medium to high boiling point, such as kerosene or diesel oil, furthermore coal tar oils and oils of vegetable or animal origin, aliphatic, cyclic and aromatic hydrocarbons, e.g. toluene, xylene, paraffin, tetrahydronaphthalene, alkylated naphthalenes or their derivatives, alcohols such as methanol, ethanol, propanol, butanol and cyclohexanol, glycols, ketones such as cyclohexanone and gamma-butyrolactone, fatty acid dimethylamides, fatty acids and fatty acid esters and strongly polar solvents, e.g. amines such as N-methylpyrrolidone.

Solid carriers are mineral earths such as silicates, silica gels, talc, kaolins, limestone, lime, chalk, bole, loess, clays, dolomite, diatomaceous earth, calcium sulfate, magnesium sulfate, magnesium oxide, ground synthetic materials, fertilizers, such as, e.g., ammonium sulfate, ammonium phosphate, ammonium nitrate, ureas, and products of vegetable origin, such as cereal meal, tree bark meal, wood meal and nutshell meal, cellulose powders and other solid carriers.

Suitable surfactants (adjuvants, wetters, tackifiers, dispersants or emulsifiers) are alkali metal, alkaline earth metal and ammonium salts of aromatic sulfonic acids, such as ligninsoulfonic acid (Borresperse® types, Borregard, Norway) phenolsulfonic acid, naphthalenesulfonic acid (Morwet® types, Akzo Nobel, U.S.A.), dibutylnaphthalene-sulfonic acid (Nekal® types, BASF, Germany), and fatty acids, alkylsulfonates, alkylarylsulfonates, alkyl sulfates, laurylether sulfates, fatty alcohol sulfates, and sulfated hexa-, hepta- and octadecanolates, sulfated fatty alcohol glycol ethers, furthermore condensates of naphthalene or of naphthalenesulfonic acid with phenol and formaldehyde, polyoxy-ethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and proteins, denatured proteins, polysaccharides (e.g. methylcellulose), hydrophobically modified starches, polyvinyl alcohols (Mowiol® types, Clariant, Switzerland), polycarboxylates (Sokolan® types, BASF, Germany), polyalkoxylates, polyvinylamines (Lupasol® types, BASF, Germany), polyvinylpyrrolidone and the copolymers thereof.

Examples for thickeners (i.e. compounds that impart a modified flowability to compositions, i.e. high viscosity under static conditions and low viscosity during agitation) are polysaccharides and organic and anorganic clays such as Xanthan gum (Kelzan®, CP Kelco, U.S.A.), Rhodopol® 23 (Rhodia, France), Veegum® (R.T. Vanderbilt, U.S.A.) or Attaclay® (Engelhard Corp., NJ, USA).

Bactericides may be added for preservation and stabilization of the composition. Examples for suitable bactericides are those based on dichlorophene and benzylalcohol hemi formal (Proxel® from ICI or Acticide® RS from Thor Chemie and Kathon® MK from Rohm & Haas) and isothiazolinone derivatives such as alkylisothiazolinones and benzisothiazolinones (Acticide® MBS from Thor Chemie).

Examples for suitable anti-freezing agents are ethylene glycol, propylene glycol, urea and glycerin.

Examples for anti-foaming agents are silicone emulsions (such as e.g. Silikon® SRE, Wacker, Germany or Rhodorsil®, Rhodia, France), long chain alcohols, fatty acids, salts of fatty acids, fluoroorganic compounds and mixtures thereof.

Suitable colorants are pigments of low water solubility and water-soluble dyes. Examples to be mentioned and the designations rhodamin B, C. I. pigment red 112, C. I. solvent red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples for tackifiers or binders are polyvinylpyrrolidons, polyvinylacetates, polyvinyl alcohols and cellulose ethers (Tylose®, Shin-Etsu, Japan). Powders, materials for spreading and dusts can be prepared by mixing or concomitantly grinding the compounds I and, if appropriate, further active substances, with at least one solid carrier. Granules, e.g. coated granules, impregnated granules and homogeneous granules, can be prepared by binding the active substances to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, e.g. ammonium sulfate, ammonium phosphate, ammonium nitrate, ureas, and products of vegetable origin, such as cereal meal, tree bark meal, wood meal and nutshell meal, cellulose powders and other solid carriers.

Examples for composition types are:

1. Composition Types for Dilution with Water i) Water-Soluble Concentrates (SL, LS)

10 parts by weight of a compound I according to the invention are dissolved in 90 parts by weight of water or in a water-soluble solvent. As an alternative, wetting agents or other auxiliaries are added. The active substance dissolves upon dilution with water. In this way, a composition having a content of 10% by weight of active substance is obtained.

ii) Dispersible Concentrates (DC)

20 parts by weight of a compound I according to the invention are dissolved in 70 parts by weight of cyclohexanone with addition of 10 parts by weight of a dispersant, e.g. polyvinylpyrrolidone. Dilution with water gives a dispersion. The active substance content is 20% by weight.

iii) Emulsifiable Concentrates (EC)

15 parts by weight of a compound I according to the invention are dissolved in 75 parts by weight of xylene with addition of calcium dodecylbenzenesulfonate and castor oil ethoxylate (in each case 5 parts by weight). Dilution with water gives an emulsion. The composition has an active substance content of 15% by weight.

iv) Emulsions (EW, EO, ES)

25 parts by weight of a compound I according to the invention are dissolved in 35 parts by weight of xylene with addition of calcium dodecylbenzenesulfonate and castor oil ethoxylate (in each case 5 parts by weight). This mixture is introduced into 30 parts by weight of water by means of an emulsifying machine (Ultraturrax) and made into a homogeneous emulsion. Dilution with water gives an emulsion. The composition has an active substance content of 25% by weight.

v) Suspensions (SC, OD, FS)

In an agitated ball mill, 20 parts by weight of a compound I according to the invention are comminuted with addition of 10 parts by weight of dispersants and wetting agents and 70 parts by weight of water or an organic solvent to give a fine active substance suspension. Dilution with water gives a stable suspension of the active substance. The active substance content in the composition is 20% by weight.

vi) Water-Dispersible Granules and Water-Soluble Granules (WG, SG)

50 parts by weight of a compound I according to the invention are ground finely with addition of 50 parts by weight of dispersants and wetting agents and prepared as water-dispersible or water-soluble granules by means of technical appliances (e.g. extrusion, spray tower, fluidized bed). Dilution with water gives a stable dispersion or solution of the active substance. The composition has an active substance content of 50% by weight.

vii) Water-Dispersible Powders and Water-Soluble Powders (WP, SP, SS, WS)

75 parts by weight of a compound I according to the invention are ground in a rotor-stator mill with addition of 25 parts by weight of dispersants, wetting agents and silica gel. Dilution with water gives a stable dispersion or solution of the active substance. The active substance content of the composition is 75% by weight.

viii) Gel (GF)

In an agitated ball mill, 20 parts by weight of a compound I according to the invention are comminuted with addition of 10 parts by weight of dispersants, 1 part by weight of a gelling agent wetters and 70 parts by weight of water or of an organic solvent to give a fine suspension of the active substance. Dilution with water gives a stable suspension of the active substance, whereby a composition with 20% (w/w) of active substance is obtained.

2. Composition Types to be Applied Undiluted ix) Dustable Powders (DP, DS)

5 parts by weight of a compound I according to the invention are ground finely and mixed intimately with 95 parts by weight of finely divided kaolin. This gives a dustable composition having an active substance content of 5% by weight.

x) Granules (GR, FG, GG, MG)

0.5 parts by weight of a compound I according to the invention is ground finely and associated with 99.5 parts by weight of carriers. Current methods are extrusion, spray-drying or the fluidized bed. This gives granules to be applied undiluted having an active substance content of 0.5% by weight.

xi) ULV solutions (UL)

10 parts by weight of a compound I according to the invention are dissolved in 90 parts by weight of an organic solvent, e.g. xylene. This gives a composition to be applied undiluted having an active substance content of 10% by weight.

The agrochemical compositions generally comprise between 0.01 and 95%, preferably between 0.1 and 90%, most preferably between 0.5 and 90%, by weight of active substance. The active substances are employed in a purity of from 90% to 100%, preferably from 95% to 100% (according to NMR spectrum).

Water-soluble concentrates (LS), flowable concentrates (FS), powders for dry treatment (DS), water-dispersible powders for slurry treatment (WS), water-soluble powders (SS), emulsions (ES) emulsifiable concentrates (EC) and gels (GF) are usually employed for the purposes of treatment of plant propagation materials, particularly seeds. These compositions can be applied to plant propagation materials, particularly seeds, diluted or undiluted. The compositions in question give, after two-to-tenfold dilution, active substance concentrations of from 0.01 to 60% by weight, preferably from 0.1 to 40% by weight, in the ready-to-use preparations. Application can be carried out before or during sowing. Methods for applying or treating agrochemical compounds and compositions thereof, respectively, on to plant propagation material, especially seeds, are known in the art, and include dressing, coating, pelleting, dusting, soaking and in-furrow application methods of the propagation material. In a preferred embodiment, the compounds or the compositions thereof, respectively, are applied on to the plant propagation material by a method such that germination is not induced, e.g. by seed dressing, pelleting, coating and dusting.

In a preferred embodiment, a suspension-type (FS) composition is used for seed treatment. Typically, a FS composition may comprise 1-800 g/l of active substance, 1 200 g/l surfactant, 0 to 200 g/l antifreezing agent, 0 to 400 g/l of binder, 0 to 200 g/l of a pigment and up to 1 liter of a solvent, preferably water.

The active substances can be used as such or in the form of their compositions, e.g. in the form of directly sprayable solutions, powders, suspensions, dispersions, emulsions, oil dispersions, pastes, dustable products, materials for spreading, or granules, by means of spraying, atomizing, dusting, spreading, brushing, immersing or pouring. The application forms depend entirely on the intended purposes; it is intended to ensure in each case the finest possible distribution of the active substances according to the invention.

Aqueous application forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active substance concentrations in the ready-to-use preparations can be varied within relatively wide ranges. In general, they are from 0.0001 to 10%, preferably from 0.001 to 1% by weight of active substance.

The active substances may also be used successfully in the ultra-low-volume process (ULV), it being possible to apply compositions comprising over 95% by weight of active substance, or even to apply the active substance without additives.

Various types of oils, wetters, adjuvants, herbicides, bactericides, other fungicides and/or pesticides may be added to the active substances or the compositions comprising them, if appropriate not until immediately prior to use (tank mix). These agents can be admixed with the compositions according to the invention in a weight ratio of 1:100 to 100:1, preferably 1:10 to 10:1.

Adjuvants which can be used are in particular organic modified polysiloxanes such as Break Thru S 240®; alcohol alkoxylates such as Atplus 245®, Atplus MBA 1303®, Plurafac LF 300® and Lutensol ON 30®; EO/PO block polymers, e.g. Pluronic RPE 2035® and Genapol B®; alcohol ethoxylates such as Lutensol XP 80®; and dioctyl sulfosuccinate sodium such as Leophen RA®.

The following examples are intended to illustrate the invention, but without imposing any limitation.

EXAMPLES

Example 1

Corn seeds (Zea mays, cultivar "Shorty") were either treated with a formulation containing pyraclostrobin (product name: Stamina®) at a rate of 5 g/100 kg seeds or they were left untreated. Seeds were planted 1 seed/pot in standard greenhouse soil (mixture of peat, loam and sand) and grown in a climate chamber at 20° C. and 60% humidity. Plants were grown for ten days in a completely randomized set-up. On day 6, plants were watered to full water holding capacity but not fertilized. Afterwards, they were left to dry out.

On day 10 (10 days after the seeds had been treated with pyraclostrobin), the plants were separated out and each pot was set onto a plant saucer designed with an inner compartment for the pot and an outer ring that is filled with water. At time 0, water with or without various concentrations of NPK fertilizer (compound B) was applied to the plant such that the water holding capacity of the soil exceeded 90%. Then a gas sampling chamber was placed over the plant saucer such that the rim fit into the ring filled with water to create a gas-tight chamber. Subsequently, 20 cubic centimeter (cc) air from the chamber were drawn into a syringe and immediately emptied into a Vacutainer (Labco, 12 ml volume). This equals the time 0 measurement for each pot. The same procedure was performed with all pots in the experiment. After one hour incubation time, again 20 cc air samples were taken from the gas chambers and emptied into Vacutainers as described above. Plants were then returned to their positions in the climate chamber. The measurements were repeated at precisely the same time of the day for the next two days. Samples were analyzed in a Shimadzu 2014 GC equipped with an ECD system.

TABLE 3

Determination of the N$_2$O increase over ambient. Results shown are peak values on day 2 of the three day measurement after treatment of controls and seed treated plants with 0.3% of the commercially available NPK fertilizer HaKaPhos ® Blue (Compo).

| Treatment | N$_2$O increase over ambient | SD |
|---|---|---|
| Untreated Control (UTC) | 190 ppbv/h | 31 |
| Pyraclostrobin (compound A) | 107 ppbv/h | 16 |

N = 14 in both cases.
SD = Standard Deviation;
ppbv = parts per billion by volume.

As can be seen from table 3, pyraclostrobin as compound (A) applied as seed treatment is able to significantly reduce the N$_2$O emission from soils when the respective fertilizer (compound B) is applied 10 days after the application of compound (A) according to the method of the invention.

Example 2

Soil samples (10 g dry weight) of various soil types (see table 4) were placed into 50 ml screw cap centrifuge tubes. Water or water containing pyraclostrobin as compound (A) as EC formulation (product name Comet®, concentration 250 g/L diluted in 200 L/ha) at a volume of 18.5 ml was added to the soil until all liquid was absorbed. Subsequently, the soil samples were left to rest for 1 day. One ml Ca(NO$_3$)$_2$ solution as a fertilizer (compound B) was added such that the final concentration of nitrate in the soil equaled 100 kg N/ha. Then 0.5 ml glucose solution (3 mg glucose per 10 mg soil) were added. Soil samples were mixed and incubated at 20° C. for 48 h.

Nitrate and ammonium content was then analyzed after adding 20 ml of a 2% K$_2$SO$_4$ solution, shaken and filtered. Measurements were done by the Conway method (Stanford et. al, 1973: Nitrate determination by a modified Conway microdiffusion method. J. Assoc. Off. Anal. Chem. 56:1365-1368). As published in Stanford et al. 1975, Soil Sci. Soc. Amer. Proc., vol. 39: 867-870, Paul and Beauchamp (1989): Can. J. Microbiol. 35:754-759, and Allgemeine Mikrobiologie, H. G. Schlegel, editor, Thieme Verlag, Stuttgart, 2006, this method is suitable for determining loss of nitrogen in the soil, and therefore indirectly the amount of N$_2$O produced in soils of various origins.

TABLE 4

Results are shown for the untreated control (UTC) (=water only) or after application of pyraclostrobin as compound (A) in different soil types.

| | Loss of NO$_3$—N + NH$_4$—N in mg N/10 g soil in 48 h | | | |
|---|---|---|---|---|
| Soil type | UTC | SD | Pyraclostrobin | SD |
| LiHof | 0.54 | 0.02 | 0.06 | 0.09 |
| Sp 2.1 | 0.16 | 0.00 | 0.03 | 0.01 |
| Sp 2.2 | 0.19 | 0.01 | 0.02 | 0.01 |
| Sp 2.3 | 0.38 | 0.01 | 0.18 | 0.05 |
| Sp 2.4 | 0.37 | 0.01 | 0.13 | 0.00 |
| Sp 5M | 0.27 | 0.02 | 0.10 | 0.02 |
| Sp 6S | 0.48 | 0.01 | 0.21 | 0.13 |

The soil types are LiHof = natural soil samples from a field site at Limburgerhof (Germany); Sp 2.1, Sp 2.2, Sp 2.3, Sp 2.4, Sp 5M and Sp 6S are commercially available soils (LUFA).

As can be seen from table 4, pyraclostrobin as compound (A) applied to various types of soil is able to significantly reduce the N$_2$O emission from soil to a varying degree when the respective fertilizer (compound B) was applied 1 day after the application of compound (A) according to the method of the invention. This reduction is especially strong when applied to a natural soil system (LiHof).

Example 3

In the same experimental set-up as described for example 2, pyraclostrobin as well as boscalid (displaying a different mode of action), were tested as compounds (A) in the soil type LiHof. The potential to reduce N$_2$O emission from soils was evaluated as described in example 2. Application rates of individual compounds are listed in table 5.

TABLE 5

| Treatment | Application rate | Loss of NO$_3$—N + NH$_4$—N in mg N/10 g soil in 48 h | SD |
|---|---|---|---|
| UTC | / | 0.52 | 0.04 |
| Pyraclostrobin | 250 g/ha | 0.09 | 0.01 |
| Boscalid | 2.33 g/L | 0.35 | 0.03 |

As can be seen from table 5, the application of pyraclostrobin or boscalid as compound (A) to soil significantly reduced the N$_2$O emission from soil when the respective fertilizer (compound B) was applied 1 day after the application of compound (A) according to the invention.

Example 4

Greenhouse trials were performed in soil samples from a field site representing the A$_h$ horizon of a pseudogleic paracambisol. Pots were filled with 10 kg of the respective soil and subsequently summer wheat was planted. A randomized set-up was established and the pots were watered to 60% water-filled pore space each day. Each sampling day the pots were enclosed in individual gas-tight sampling chambers at the same time each day and three gas samples were taken over an incubation time of 90 min. Pots were either treated with pyraclostrobin (250 g/ha=50 ml of 17.32 mg/l solution) or left untreated (UTC=water only). Fertilizer (ammonium nitrate (compound B) to a concentration of 100 kg/ha) was applied as shown in table 6. Samples were taken over a period of 4 weeks.

TABLE 6

| Treatment | Mean mg N$_2$O—N/m$^2$ | SEM |
|---|---|---|
| UTC | 83.0 | 30.0 |
| Fertilizer (ammonium nitrate) | 291.6 | 39.1 |
| Pyraclostrobin together with the application of the fertilizer | 314.9 | 167.0 |
| Pyraclostrobin 8 days before the application of the fertilizer | 100.9 | 31.7 |

Table 6 clearly shows the surprising technical effect of the current invention. Unexpectedly it was found that the application of pyraclostrobin as compound (A) and ammonium nitrate as compound (B) when carried out with a time lag of at least 1 day (in this case 8 days), the N$_2$O emission from soils is significantly reduced compared to the application of a fertilizer (compound B) alone or when a compound (A) was applied together with a compound (B). Consequently, it could be shown that a combined application of compound (A) and compound (B) does not result in a reduction of N$_2$O emission from soils while the separate application of compound (A) and compound (B) with a time lag of at least one day surprisingly results in a strong reduction of nitrous oxide emission from soils.

The invention claimed is:

1. A method for reducing nitrous oxide emission from soils comprising:
    treating seeds from which a plant grows by applying at least one fungicide compound (A) selected from inhibitors of complex III at Qo site selected from the group consisting of pyraclostrobin, orysastrobin, azoxystrobin, dimoxystrobin, enestroburin, fluoxastrobin, kresoxim-methyl, metominostrobin, picoxystrobin, pyribencarb and trifloxystrobin; and
    applying at least one ammonium- or urea-containing fertilizer compound (B) selected from the group consisting of:
    (B1) inorganic fertilizer selected from the group consisting of:
        NPK fertilizer, ammonium nitrate, calcium ammonium nitrate, ammonium sulfate nitrate, ammonium sulfate and ammonium phosphate; and
    (B2) organic fertilizer selected from the group consisting of:
        liquid manure, semi-liquid manure, stable manure and straw manure, worm castings, compost, seaweed and guano;
    wherein the applications of at least one compound (A) is carried out in the absence of compound (B) and the application of at least one compound (B) is carried out in the absence of further application of compound (A) and with a lag time of at least 8 days, and wherein compound (A) is applied as a seed treatment in amounts of from 0.05 g to 2 g per kg of seed.

2. The method according to claim 1, wherein compound (A) is pyraclostrobin.

3. The method according to claim 1, wherein the at least one compound (A) applied is at least two compounds (A).

4. The method according to claim 1, wherein the plant is selected from the group consisting of agricultural, silvicultural, ornamental and horticultural plants, each in its natural or genetically modified form.

5. The method according to claim 4, wherein the plant is selected from the group consisting of wheat, barley, oat, rye, soybean, corn, oilseed rape, canola, sunflower, cotton, sugar cane, sugar beet, rice and sorghum.

6. The method of claim 1, wherein compound (A) is selected from the group consisting of azoxystrobin, pyraclostrobin, and trigloxystrobin.

7. The method of claim 1, wherein the application rate of compound (B) is between 10 kg and 300 kg of N per hectare.

8. The method of claim 3, wherein the at least two compounds (A) are pyraclostrobin and trigloxystrobin.

9. The method of claim 1, wherein compound (B) is selected from the group consisting of ammonium sulfate nitrate and ammonium sulfate.

10. The method of claim 1, wherein the at least one compound (B) is applied to the plant or the locus where the plant is growing or is intended to grow.

11. The method of claim 3, wherein the at least two compounds (A) are pyraclostrobin and azoxystrobin.

* * * * *

UNITED STATES PATENT AND TRADEMARK OFFICE
CERTIFICATE OF CORRECTION

PATENT NO. : 8,956,996 B2  Page 1 of 1
APPLICATION NO. : 13/496218
DATED : February 17, 2015
INVENTOR(S) : Markus Gewehr et al.

It is certified that error appears in the above-identified patent and that said Letters Patent is hereby corrected as shown below:

In the Claims

Column 25, line 23, claim 1, please change "applications" to --application--.

Signed and Sealed this
Sixteenth Day of June, 2015

Michelle K. Lee
*Director of the United States Patent and Trademark Office*